Figure 1:
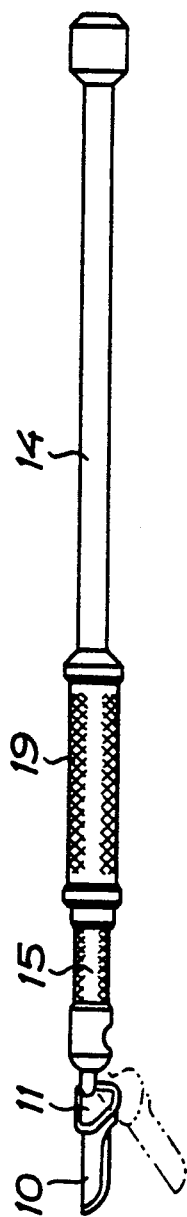

United States Patent [19]

Lundgren

[11] Patent Number: 5,055,106
[45] Date of Patent: Oct. 8, 1991

[54] SCALPEL

[76] Inventor: Dan Lundgren, Askims Kyrkväg 5, S-430 80 Hovås, Sweden

[21] Appl. No.: 571,620
[22] PCT Filed: Feb. 27, 1989
[86] PCT No.: PCT/SE89/00084
  § 371 Date: Sep. 7, 1990
  § 102(e) Date: Sep. 7, 1990
[87] PCT Pub. No.: WO89/08429
  PCT Pub. Date: Sep. 21, 1989

[30] Foreign Application Priority Data

Mar. 9, 1988 [SE] Sweden .............................. 8800833

[51] Int. Cl.$^5$ ............................................ A61B 17/32
[52] U.S. Cl. ...................................... 606/167; 30/321; 30/338
[58] Field of Search .................. 606/167, 170; 30/321, 30/339, 330, 331, 336, 337, 338; 403/90

[56] References Cited

U.S. PATENT DOCUMENTS

| | | | |
|---|---|---|---|
| 2,425,665 | 8/1947 | Arden | 403/90 |
| 3,609,864 | 10/1971 | Bassett | 30/321 |
| 4,275,735 | 6/1981 | Chutter | 606/167 |
| 4,672,964 | 6/1987 | Dee et al. | 606/167 |
| 4,788,070 | 12/1986 | Dee | 606/167 |
| 4,844,976 | 7/1989 | Dee | 606/167 |

FOREIGN PATENT DOCUMENTS 1264265 5/1961 France .
490072 5/1970 Switzerland .

Primary Examiner—C. Fred Rosenbaum
Assistant Examiner—William W. Lewis
Attorney, Agent, or Firm—Berman & Aisenberg

[57] ABSTRACT

A scalpel comprises a shank having a holder for releasably mounting a surgical blade. A ball of plastic material is formed by injection molding on the blade proper which consists of metal. The holder includes a sleeve, which is threadedly engaged with the shank at one end thereof and adapted to be screwed axially along the shank. The sleeve forms a ball socket, which is adapted to receive the ball of the blade therein. A clamping rod extends axially within the socket between the shank and the ball to engage and disengage said ball by the sleeve being screwed on the shank. The end of the clamping rod, which is adjacent to the ball, forms a circular sharp edge of a diameter which is substantially smaller than the diameter of the ball, thus cutting into the plastic material of the ball when the sleeve is screwed to engage the clamping rod with said ball.

9 Claims, 1 Drawing Sheet

SCALPEL

The invention relates to a scalpel comprising a shank having a holder for releasably mounting a surgical blade, said holder including a sleeve threadedly engaged with the shank at one end thereof to be screwed axially along the shank and forming a ball socket, a ball on the blade to be received in said ball socket, and a clamping rod extending axially within the socket between the shank and the ball to engage and disengage said ball by the sleeve being screwed on the shank.

A scalpel of this type is shown and described in CH-A-490 072. The rod projecting from the shank and being integral therewith, at the free end forms a seat which can be engaged with and can partially receive therein the ball of the blade by screwing the sleeve on the shank so that the ball will be clamped in the ball socket. The ball and the ball socket form a universal joint which allows the blade to be adjusted to different angles on the shank and to be locked in the desired angular position.

Many types of surgery cause specific access problems, and this is particularly true as far as oral surgery is concerned (gingival operations, extraction of wisdom-teeth etc), joint surgery and surgical intervention in ears, nose and throat. In these cases it may be difficult to obtain access by means of a common straight scalpel. It may be necessary to use angled scalpels or reversed knives which are used for example in gingival operations. Scalpels of the type mentioned above have been proposed in order to allow extraordinary access in different surgical operations of any type.

In the prior art scalpel referred to above the ball and thus the blade is locked in the desired angular position by the frictional engament between the ball at one hand and the seat of the rod and the ball socket at the other hand, and accordingly it is necessary to securely tighten the sleeve on the shank to be sure that the angular position of the blade will not change or the blade will come loose when the scalpel is being used.

The purpose of the present invention is to provide a scalpel of the type referred to above wherein the blade is more securely anchored to the shank in the desired angular position, which is an absolute central requirement in oral surgery wherein an instrument of this type definitely shall not be allowed to come loose.

For said purpose the scalpel of the invention has obtained the characteristic features appearing from claim 1.

Figure 2:
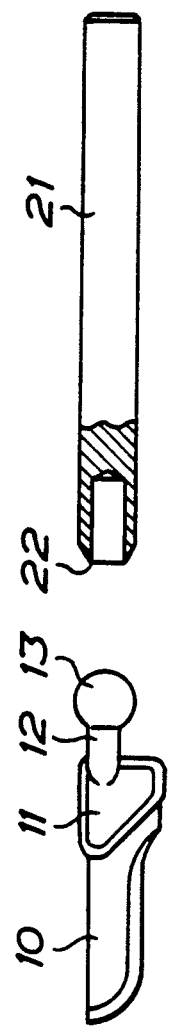
Figure 3:
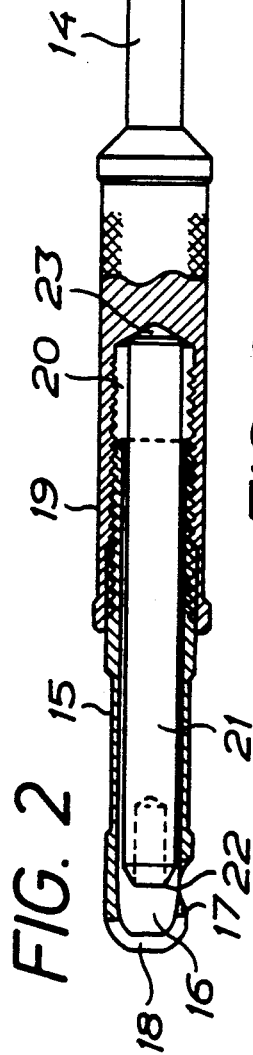
Figure 4:
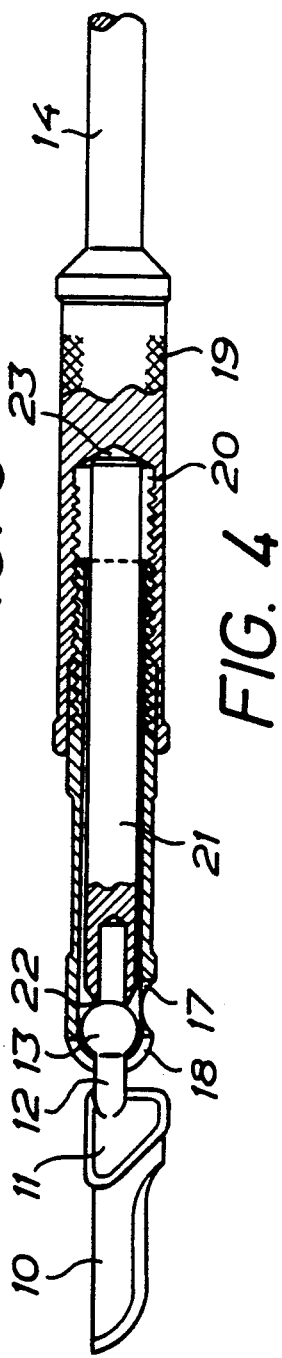

In order to explain the invention in more detail an embodiment thereof will be described below reference being made to the accompanying drawing in which FIG. 1 is a side view of a scalpel of the invention, FIG. 2 is an enlarged side view of the blade and an element forming the circular sharp edge to be engaged with the ball, said element being partly shown in axial cross sectional view, FIG. 3 is a fragmentary enlarged axial cross sectional view of the blade end of the scalpel without the blade, and FIG. 4 is a view similar to that in FIG. 3 with the blade mounted to the shank.

The surgical blade shown in the drawing comprises a metal portion 10 forming the actual blade (the knife edge), and on this metal portion a plastic body 11 is formed by injection molding, said plastic body forming a neck 12 and a ball 13. On the shank 14 of the scalpel there is provided for the attachment of the blade a sleeve 15 which forms a spherical ball socket 16 available from the outside through a side aperture 17. Moreover, the sleeve has a slot 18 joining the aperture 17. The sleeve is threadedly engaged with the shank, and for this purpose the shank forms a thicker end portion 19 with a bore 20 having an inside screw thread. The sleeve 15 having an outside screw threadedly engages the inside screw thread of the portion 19 and can be displaced axially into and out of the bore by the sleeve being rotated and thus being screwed on the shank. In the sleeve a clamp rod 21 is received, and this rod has at the end adjacent the ball socket a circular sharp edge 22, FIG. 2, having a diameter which is considerably smaller than the diameter of the ball 13. The other end of the clamp rod can be engaged with an abutment surface 23 formed by the shank at the bottom of the bore.

The ball 13 on the blade can be inserted into the ball socket 16 passing through the side aperture 17. The ball can be freely rotated in the ball socket for the adjustment of the blade to a desired rotated or angled position the neck 12 being received by the slot 18 at angling, and can be locked with the blade in the desired position by screwing the sleeve 15 axially on the shank so that the circular sharp edge 22 of the clamp rod will be engaged with the ball and will cut into the plastic material of the ball the clamp rod being supported by the abutment surface 23. The hardness of the plastic material (preferably carbon fibre reinforced plastic material) must of course be chosen such that it is lower than the hardness of the material of the clamp rod, usually metal, so that it is possible for the edge of the clamp rod to cut into the material. The blade 10 can be rapidly locked in the desired position and in the desired angle "around the horizon" over about ⅝ of an imagined sphere. Since the blade can be rotated over 360 degrees and can be given the proper direction in all conceivable positions the need of having several scalpels of different types will be eliminated. If it is desired to change slightly the angular position in which the blade has been locked this can easily be done. The sharp edge of the clamping rod will cut into the ball in the new position without any risk of the clamping rod positively moving the ball back to the previous position as could happen if the clamping rod engaged the ball at a solid end and made only a depression in the ball. In that case the clamping rod may tend to land at the bottom of the depression made in the previous position thereby causing slight rotation of the ball to said position.

Due to the stepless adjustment of the blade in a desired plane and in a desired angle the incision in many regions will be facilitated, the extreme access in the oral cavity and other cavities in the body will be achieved. The surgical blade of the invention due to the fact that the attachment portion thereof comprises a plastic portion formed thereon by injection molding can be manufactured at very low costs so that the blade is a cheap one-way product and thus can be replaced at low costs when necessary and will be securely anchored in the position of use thereof.

Preferably the plastic body consists of a plastic material which can be sterilized, and the shank, sleeve and clamp rod consist of stainless steel.

I claim:

1. A scalpel comprising a shank having a holder for releasably mounting a surgical blade, the surgical blade, said holder including a sleeve threadedly engaged with the shank at one end thereof adapted to be screwed axially along the shank and forming a ball socket, a ball of plastic material on said blade adapted to be received in said ball socket, and a clamping rod extending axially within the socket between the shank and the ball adapted to engage and disengage said ball by the sleeve being screwed on the shank, characterized in that the end of the clamping rod, which is adjacent the ball, forms a circular sharp edge which faces the ball axially and has a diameter substantially smaller than the diameter of the ball, thus being adapted to cut into the plastic material of the ball at said edge when the sleeve is screwed to engage the clamping rod with said ball.

2. A scalpel as in claim 1 wherein the sleeve is screwed into a bore formed by the shank.

3. Scalpel as in claim 2 wherein the clamp rod as a separate element is received by the sleeve and said bore to be engaged between the ball and an abutment surface formed by the shank at the bottom of the bore.

4. A scalpel comprising a shank, a clamp rod, a sleeve, and a surgical blade;
the surgical blade comprising a metal portion and a plastic body with a neck which joins the metal portion to a ball;
the shank having a substantially hollow thicker end portion with an inner abutment surface;
the sleeve having, at one end, a spherical ball socket and an adjacent side aperture; and
means to secure the clamp rod tightly between the inner abutment surface and the surgical blade ball when said ball is in the spherical ball socket, the means comprising external threads on said sleeve and matching internal threads on the substantially hollow-end portion of said shank; and
said clamp rod having an end, remote from said inner abutment surface, with a circular sharp edge which faces the surgical blade ball axially and has a diameter substantially smaller than that of said surgical blade ball.

5. A scalpel of claim 1 wherein the clamp rod is so tightly held between the inner abutment surface and the surgical blade ball that the circular sharp edge of said clamp rod cuts into the plastic of said ball.

6. A scalpel of claim 4 wherein the plastic body of the surgical blade is injection molded on the metal portion thereof.

7. A scalpel comprising a shank, a holder on said shank, said holder including a sleeve threadedly engaged with the shank at one end thereof and adapted to be screwed axially along the shank and forming a ball socket, a surgical blade of metal, a ball of plastic material formed by injection molding on the blade and adapted to be received in said ball socket for releasably mounting the blade to the shank, a clamping rod extending axially within the socket between the shank and the ball and adapted to engage and disengage said ball by the sleeve being screwed on the shank; the end of the clamping rod, which is adjacent the ball, forming a circular shape edge which faces the ball axially and has a diameter substantially smaller than the diameter of the ball, being adapted to cut into the plastic material of the ball at said edge when the sleeve is screwed to engage the clamping rod with said ball.

8. A scalpel as in claim 7 wherein the shank forms a bore, the sleeve being screwed into said bore.

9. A scalpel as in claim 8 wherein the shank forms an abutment surface at the bottom of said bore, the clamp rod as a separate element being received by the sleeve and said bore to be engaged between the ball and said abutment surface.

* * * * *